United States Patent [19]

Shen et al.

[11] Patent Number: 4,656,190

[45] Date of Patent: Apr. 7, 1987

[54] INDENE DERIVATIVES AND THEIR USE AS PAF-ANTAGONISTS

[75] Inventors: Tsung-Ying Shen, Westfield; Shu S. Yang, Bridgewater; San-Bao Hwang, Scotch Plains, all of N.J.

[73] Assignee: Merck & Co., Inc., Rahway, N.J.

[21] Appl. No.: 550,839

[22] Filed: Nov. 14, 1983

[51] Int. Cl.⁴ .......................................... C07D 257/04
[52] U.S. Cl. .................................. 514/529; 514/602; 514/311; 514/396; 514/381; 560/10; 564/85; 548/335; 548/252; 546/216; 544/248
[58] Field of Search .................. 564/85; 424/309; 560/10; 514/529, 602

[56] References Cited

U.S. PATENT DOCUMENTS

| | | |
|---|---|---|
| 3,654,349 | 4/1972 | Shen et al. ............................ 564/85 |
| 3,737,455 | 6/1973 | Shen et al. ............................ 564/85 |
| 3,822,310 | 7/1974 | Shen et al. ............................ 564/85 |
| 3,882,239 | 6/1975 | Shen et al. ............................ 564/85 |
| 3,932,498 | 1/1976 | Shen et al. ............................ 564/85 |
| 4,087,549 | 2/1978 | Shen et al. ............................ 564/85 |

*Primary Examiner*—Glennon H. Holrah
*Assistant Examiner*—D. B. Springer
*Attorney, Agent, or Firm*—Theresa Y. Cheng; Mario A. Monaco

[57] ABSTRACT

Indene derivatives have been found to have potent and specific PAF (Platelet-Activating-Factor) antagonistic activities and are thereby useful in the treatment of various diseases or disorders mediated by the PAF, for example, inflammation, cardiovascular disorder, asthma, lung edema, and adult respiratory distress syndrome.

9 Claims, No Drawings

INDENE DERIVATIVES AND THEIR USE AS PAF-ANTAGONISTS

BACKGROUND OF THE INVENTION

Platelet-activating factor (PAF) has recently been identified as an acetyl glyceryl ether phosphorylcholine (AGEPC), i.e., 1-O-hexadecyl/octadecyl-2-O-acetyl-sn-glyceryl-3-phosphorylcholine (Hanahan, D. S. et al., J. Biol. Chem., 255: 5514, 1980). Even before its chemical identification, PAF has been linked to various biologic activities and pathways making it one of the important mediators responsible for a variety of physiological processes including activation or coagulation of platelets, pathogenesis of immune complex deposition, smooth muscle contraction, inflammation as well as respiratory, cardiovascular and intravascular alterations. These physiological processes are known to be associated with a large group of diseases, for example, inflammatory diseases, cardiovascular disorders, asthma, lung edema, and adult respiratory distress syndrome. It is therefore only natural that more and more scientific investigators are focusing their work on the search of a PAF-antagonist or inhibitor for the treatment and/or the prevention of these common diseases.

The compounds of the present invention are potent and specific PAF-antagonists. They include various substituted 1-benzylidene-indene derivatives of Structure (I) especially where $R^2$ is an amino sulfonyl group.

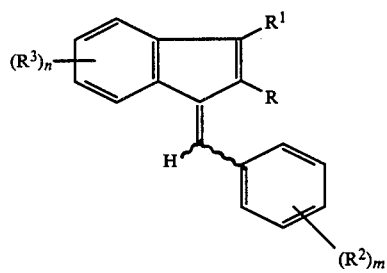

These indene derivatives are related to sulindac, a non-steroidal anti-inflammatory drug disclosed by U.S. Pat. Nos. 3,654,349; 3,870,753 and 3,994,600. However, these patents do not disclose the indene derivatives as PAF antagonists nor do they describe the 1-(p-aminosulfonylbenzylidine)-derivatives of the present invention.

Accordingly, it is the object of the present invention to provide novel derivatives of Structure (I) as specific PAF-antagonists.

Another object of this invention is to provide processes for the preparation of novel derivatives of Structure (I).

A further object of this invention is to provide a pharmaceutically acceptable composition containing at least one of the compounds of Structure (I) as the active ingredient for the treatment of diseases which are subject to the mediation of a PAF-antagonist.

Still a further object of this invention is to provide a method of treatment comprising the administration of a therapeutically sufficient amount of at least one of the compounds of Structure (I) to a patient suffering from various skeletal-muscular disorders including but not limited to inflammation, e.g., osteoarthritis, rheumatoid arthritis and gout, hypertension; cardiovascular disorder; asthma; bronchitis; lung edema; or adult respiratory distress syndrome.

DETAILED DESCRIPTION OF THE INVENTION

A. Scope of the Invention

This invention relates to specific PAF-antagonists of the structural formula (I)

wherein
R is H or loweralkyl especially $C_{1-6}$ alkyl, for example, methyl, ethyl, isopropyl, n-propyl, butyl, pentyl or hexyl;

$R^1$ is
(a) —$CHR^4COOR$ wherein $R^4$ is hydrogen or loweralkyl;
(b) —$(CH_2)_mR^5$ wherein $R^5$ represents R, OR, SR, S-phenyl(unsubstituted or substituted), SOR, $SO_2R$, —O—COR, —NHCOR, —$NRR^4$, halo especially fluoro; and m is 1 to 4;
(c) —CH=CHR;
(d) —$CH_2CONRR^4$; or
(e) —CHOH—CHOH—R;

$R^2$ is
(a) —$NHSO_2R^6$ where $R^6$ represents R, —$CF_3$, unsubstituted or substituted phenyl, for example, phenyl, p-methoxyphenyl, p-chlorophenyl, m-trifluoromethylphenyl or the like;
(b) hydrogen;
(c) lower alkyl;

(d) $-NH\overset{\overset{O}{\|}}{C}-R^6$;

(e) —$NRR^4$;
(f) —$OR^7$ wherein $R^7$ is H, R, loweralkenyl especially $C_{1-6}$ alkenyl such as —$CH_2$—CH=$CH_2$; lower alkynyl especially $C_{1-6}$ alkynyl such as —$CH_2$—C≡CH;
(g) —$(CH_2)_mO$— when two adjacent $R^2$ are joined together and where m represents 2 or 3;
(h) halo especially fluoro, chloro and bromo;
(i) —$SR^6$;
(j) —$SOR^6$;
(k) —$SO_2R^6$;
(l) —$SO_2NRR^4$;

(m) —SO$_2$NHY wherein Y is a heterocycle as defined below;
(n) —SO$_2$NHX wherein X is —CONH$_2$, CSNH$_2$ or —C(=NH)NH$_2$;
(o) —SO$_2$CF$_3$;
(p) —CN;
(q) —SO$_2$NR$^4$COR$^6$; or
(r) —COOR$^6$;

n is 1, 2 or 3; and
R$^3$ is
(a) hydrogen;
(b) lower alkyl especially C$_{1-6}$alkyl;
(c) —OR$^7$;
(d) —O—(CH$_2$)$_m$— when two adjacent R$^3$ are joined together and wherein m is 2 or 3;
(e) halo especially F;
(f) —O—CH$_2$—phenyl or substituted phenyl;
(g) —CH$_2$OR$^6$;
(h) —SR$^6$;
(i) —S—CH$_2$—phenyl or substituted phenyl;
(j) —CH$_2$—S—R$^6$;
(k) —SOR$^6$;
(l) —SO$_2$R$^6$;
(m) —OCOR$^6$;
(n) —NRR$^4$ or —NH$_2$;
(o) —NR$^4$COOR$^6$;
(p) —NHCOR$^6$; or
(q) —OCOOR$^6$.

Preferably, the specific PAF-antagonists of this invention are of the structural Formula (II)

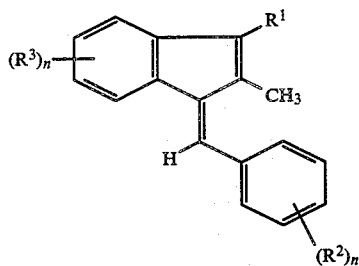

wherein R$^1$, R$^2$ and R$^3$ are as previously defined.

Even more preferably, the specific PAF-antagonists of this invention are of the structural Formula (III)

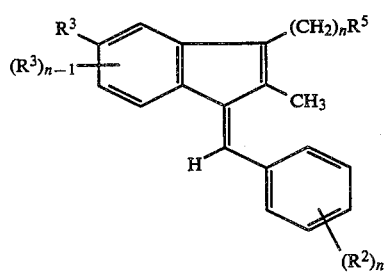

wherein
n and R$^5$ are as previously defined;
R$^2$ is
(a) —SO$_2$NRR$^4$;
(b) —SOR$^6$;
(c) —SO$_2$R$^6$;
(d) —SO$_2$NHX wherein X represents —CONH$_2$, —CSNH$_2$, —C(=NH)NH$_2$—SO$_2$NHY wherein Y represents a heterocycle e.g.,

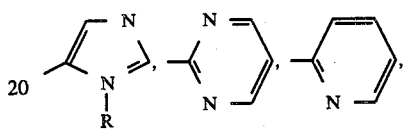

(e) —SO$_2$CF$_3$;
(f) —SO$_2$NHCOR$^6$; or
(g) —OR$^7$; and
R$^3$ is
(a) hydrogen;
(b) loweralkyl;
(c) —OR$^7$;
(d) —O(CH$_2$)$_m$— when two adjacent R$^3$ are joined together and m is 2 or 3;
(e) —OCH$_2$—phenyl or substituted phenyl;
(f) —F;
(g) —SR$^6$;
(h) —OCOR$^6$;
(i) —NHCOR$^6$; or
(j) —OCOOR$^6$.

B. Preparation of the compounds within the scope of the invention

As discussed above, most PAF-antagonists of this invention are known compounds related to sulindac except where R$^2$ is —OR$^7$, —SO$_2$NRR$^4$, SO$_2$NHC(NH)NH$_2$, SO$_2$NHCONH$_2$, and SO$_2$NR$^4$COR$^6$. These analogs, however, can be easily prepared from the corresponding indenes and the appropriately substituted benzaldehydes. For example,

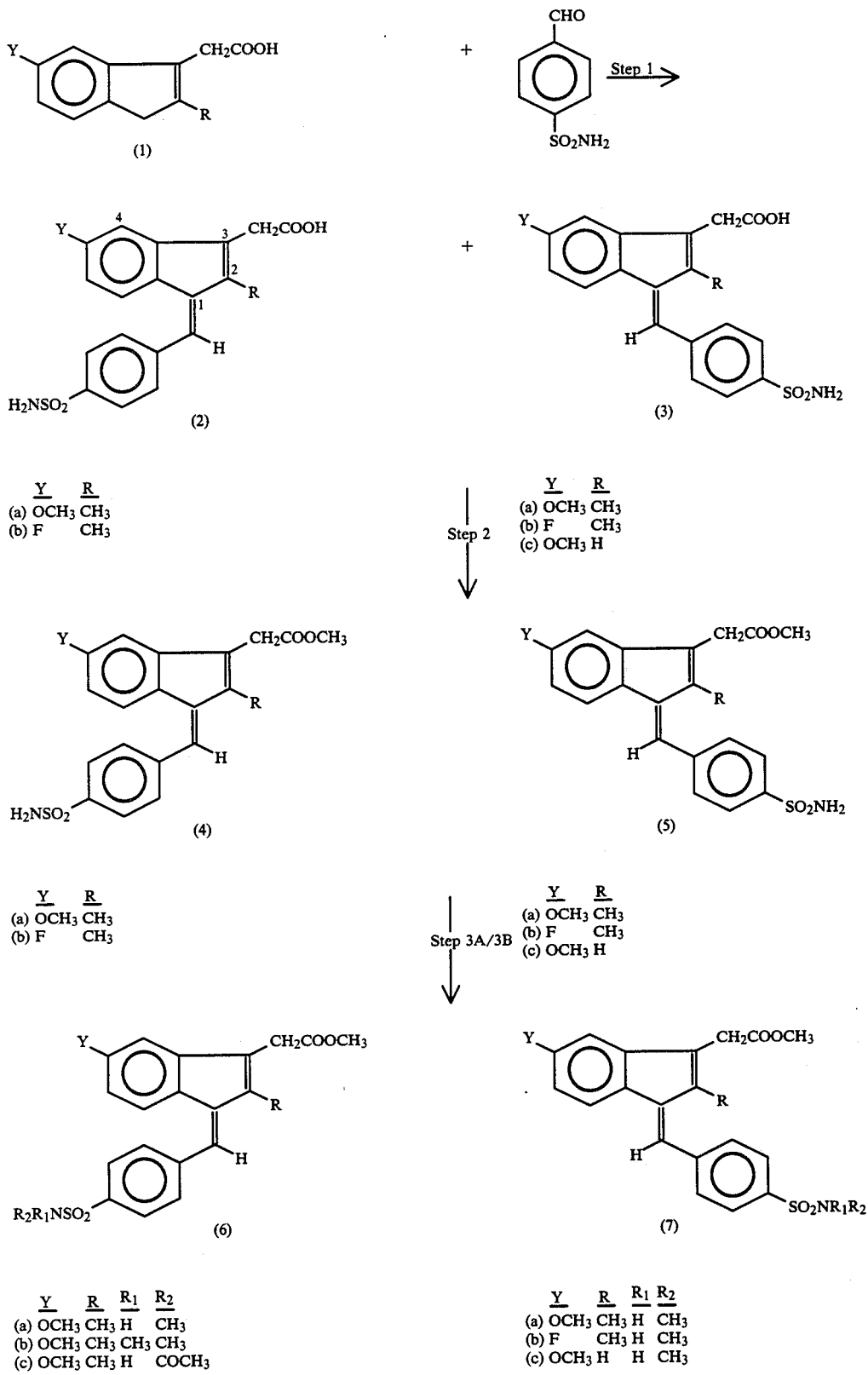

-continued
SCHEME 1

As illustrated by Example 1

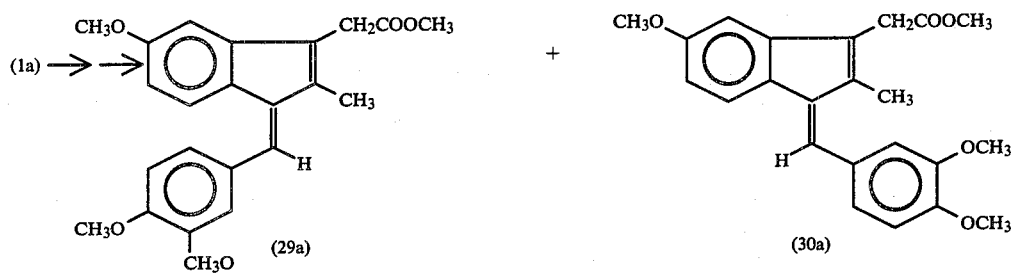

(29a)      (30a)

EXAMPLE 1

Z(cis) and E(trans) 1-(4-Aminosulfonylphenyl)methylene-5-substituted-2-methyl-1H-3-indenylacetic acids and analogs

Step 1

Preparation of E and Z 1-(4-aminosulfonylphenyl)methylene-5-methoxy-2-methyl-1H-3-indenylacetic acids (2a and 3a)

To a solution of 5-methoxy-2-methyl-3-indenylacetic acid (1a) (3.95 g) in 90% methanol (24 ml) containing 85% potassium hydroxide (2.7 g) was added a solution of p-aminosulfonylbenzaldehyde (3.70 g) in 90% methanol (24 ml). The resulting mixture was refluxed under nitrogen for 4–6 hours. A solution of 50% aqueous acetic acid (50 ml) was then added to the reaction mixture during 40 minutes at 50°–60° C. The crystals were collected after aging at 15° C. for 1 hour. The crude product was recrystallized five times from acetone-hexane to give pure Z form of 1-(4-aminosulfonylphenyl)-methylene-5-methoxy-2-methyl-1H-3-indenylacetic acid (2a) (4.0 g, 57%): m.p. 224°–225° C.; $R_f$=0.45 (silica gel, 10% MeOH in CHCl$_3$ developed 3–4 times).

Anal. Calcd for $C_{20}H_{19}NO_5S$: C, 62.33; H, 4.97; N, 3.63; S, 8.32. Found: C, 62.48; H, 5.06; N, 3.60; S, 8.15.

The E acid enriched mother liquor from above (E:Z=1:4, 100 mg) was purified via preparative tlc using 500 μm silica gel plates (3–4 mg per plate) developed 5–6 times with 10% methanol in chloroform to give the E form of 1-(4-aminosulfonylphenyl)methylene-5-methoxy-2-methyl-1H-3-indenyl acetic acid (3a); m.p. 223°–225° C.; $R_f$=0.35 (silica gel, 10% MeOH in CHCl$_3$ developed 3–4 times); mass spectrum, m/e 385; nmr (300 MHz, CD$_3$OD) δ1.80 (s, 3H, C-2-Me), (for cis C-2-Me: 2.18).

Step 2

Preparation of E and Z methyl 1-(4-aminosulfonylphenyl)methylene-5-methoxy-2-methyl-1H-3-indenylacetate (4a and 5a)

A solution of the E acid 3a (950 mg) and toluenesulfonic acid monohydrate (200 mg) in methanol (60 ml) was refluxed for 1–2 hours. The solution was filtered and the filtrate was concentrated to 30 ml. After cooling at 0° to 5° for 1 hour, the crystals were collected and dried. The crude ester was recrystallized from acetonitrile to give the pure E methyl 1-(4-aminosulfonyl-phenyl)methylene-5-methoxy-2-methyl-1H-3-indenylacetate 5a (850 mg, 86%): m.p. 169.5°–171.0° C.

Anal. Calcd for $C_{21}H_{21}NO_5S$: C, 63.14; H, 5.30; N, B 3.51; S, 8.03. Found: C, 62.97; H, 5.27; N, 3.66; S, 8.19.

In the same manner, the Z acid 2a was converted to the Z methyl 1-(4-aminosulfonylphenyl)methylene-5-methoxy-2-methyl-1H-3-indenylacetate (4a): m.p. 179.5°–181.0° C.

Anal. Calcd for $C_{21}H_{21}NO_5S$: C, 63.14; H, 5.30; N, 3.51; S, 8.03. Found: C, 63.02; H, 5.35; N, 3.37; S, 7.91.

Following substantially the same procedures as described in Steps 1 and 2, but starting with 5-fluoro-2-methyl-3-indenylacetic acid, the following analogs were prepared:

(1) Z1-(4-Aminosulfonylphenyl)methylene-5-fluoro-2-methyl-1H-3-indenylacetic acid (2b); m.p. 242.5°–244.0° C.

Anal. Calcd for $C_{19}H_{16}FNO_4S$: C, 61.12; H, 4.32; N, 3.75; F, 5.09; S, 8.59. Found: C, 61.05; H, 4.43; N, 3.61; F, 5.09; S, 8.31.

(2) Z Methyl 1-(4-aminosulfonylphenyl)methylene-5-fluoro-2-methyl-1H-3-indenylacetate (4b); m.p. 183°–184° C.

Anal. Calcd for $C_{19}H_{16}FNO_4S$: C, 62.01; H, 4.68; N, 3.62; F, 4.90; S, 8.28. Found: C, 62.11; H, 4.69; N, 3.70; F, 5.17; S, 8.35.

(3) E-Methyl 1-(4-aminosulfonylphenyl)methylene-5-fluoro-2-methyl-1H-3-indenylacetate (5b); m.p. 206.5°–208.5° C.

Anal. Calcd for $C_{20}H_{18}FNO_4S$: C, 62.01; H, 4.68; N, 3.62; F, 4.90; S, 8.28. Found: C, 61.60; H, 4.54; N, 3.52; F, 5.12; S, 8.46.

Step 3a

N-Methylation of 4a and 5a with diazomethane to form methyl 1-(4-(N-methylaminosulfonyl)phenyl)methylene-5-methoxy-2-methyl-1H-3-indenylacetate and its N,N-dimethyl derivative A solution of 4a (100 mg) in methanol (20 ml) was treated with excess diazomethane ether solution to give two products. They are separated via preparative tlc using 1500 μm silica gel plates developed 3 times with 5% ethyl acetate in chloroform to give Z methyl 1-(4-(N-methylaminosulfonyl)phenyl)methylene-5-methoxy-2-methyl-1H-3-indenylacetate (6a) (30 mg, 29% yield): m.p. 167°–169° C.

Anal. Calcd for $C_{22}H_{23}NO_5S \cdot \frac{1}{2}H_2O$: C, 62.54; H, 5.73; N, 3.31; S, 7.59. Found: C, 62.55; H, 5.52; N, 3.27; S, 7.65.

and Z methyl 1-(4-(N,N-dimethylaminosulfonyl)-phenyl)methylene-5-methoxy-2-methyl-1H-3-indenylacetate (6b) (60 mg, 56% yield): m.p. 163°–164° C.

Anal. Calcd for $C_{23}H_{25}NO_5S \cdot 1/5H_2O$: C, 64.08; H, 5.94; N, 3.25; S, 7.44. Found: C, 64.02; H, 5.91; N, 3.15; S, 7.30.

Following the same procedure as described in Step 3a but starting with 5a or 5b, the following compounds were prepared:

(1) E Methyl 1-(4-(N-methylaminosulfonyl)phenyl)-methylene-5-methoxy-2-methyl-1H-3-indenylacetate (7a): m.p. 151.5°–153.5° C.

Anal. Calcd for $C_{22}H_{23}NO_5S$: C, 63.90; H, 5.61; N, 3.39; S, 7.75. Found: C, 64.00; H, 5.65; N, 3.27; S, 7.66.

(2) E Methyl 1-[4-(N-methylaminosulfonyl)phenyl]-methylene-5-fluoro-2-methyl-1H-3-indenylacetate (7b): m.p. 168.5°–170.0° C.

Anal. Calcd for $C_{21}H_{20}FNO_4S.1/5H_2O$: C, 62.27; H, 5.08; N, 3.46. Found: C, 61.99; H, 4.64; N, 3.25.

Step 3b

Acetylation of 4a to form Z methyl 1-[4-(N-acetylaminosulfonyl)phenyl]methylene-5-methoxy-2-methyl-1H-3-indenylacetate (6c)

A solution of 4a (100 mg) in pyridine (5 ml) was added acetic anhydride (2 ml). The mixture was heated at 110° for 1 hour and concentrated in vacuo. The crude mixture was purified via preparative tlc using 2000 μm silica gel plates developed with 30% ethyl acetate in chloroform. The isolated product was recrystallized from acetone-hexane to give pure Z methyl 1-[4-(N-acetylaminosulfonyl)phenyl]methylene-5-methoxy-2-methyl-1H-3-indenylacetate (55 mg, 50%): m.p. 172.5°–174.5° C.

Anal. Calcd for $C_{23}H_{23}NO_6S$: C, 62.57; H, 5.25; N, 3.17; S, 7.26. Found: C, 62.69; H, 5.25; N, 3.15; S, 7.25.

Following the same procedure as described in Steps 1-3, but starting with an appropriate substrate, there were prepared the following compounds:

(1) From 5-methoxy-2-methyl-1H-3-indenylacetic acid and 3,4-dimethoxybenzaldehyde to Z methyl 1-(3,4-dimethoxyphenyl)methylene-5-methoxy-2-methyl-1H-3-indenylacetate (29a); m.p. 101°–103° C. and E methyl 1-(3,4-dimethoxyphenyl)methylene-5-methoxy-2-methyl-1H-3-indenylacetate (30 a); m.p. 131°–133° C.

(2) From treating 5-methoxy-1H-3-indenylacetic acid and 4-aminosulfonylbenzaldehyde to the following compounds:

(a) E 1-(4-aminosulfonylphenyl)methylene-5-methoxy-1H-3-indenylacetic acid (3c); m.p. 211°–213° C.

Anal. Calcd for $C_{19}H_{17}NO_5S.\frac{1}{2}H_2O$: C, 61.07; H, 4.65; N, 3.75. Found: C, 60.86; H, 4.54; N, 3.59.

(b) E Methyl 1-(4-aminosulfonylphenyl)methylene-5-methoxy-1H-3-indenylacetate (5c); m.p. 174°–176° C.

Anal. Calcd for $C_{20}H_{19}NO_5S$: C, 62.33; H, 4.97; N, 3.63; S, 8.31. Found: C, 62.29; H, 4.96; N, 3.35; S, 8.35.

(c) E Methyl 1-[4-(N-methylsulfonylphenyl)methylene-5-methoxy-1H-3-indenylacetate (7c); m.p. 151°–152.5° C.

Anal. Calcd for $C_{21}H_{21}NO_5S.\frac{1}{2}H_2O$: C, 61.75; H, 5.43; N, 3.43. Found: C, 61.42; H, 5.16; N, 3.13.

SCHEME II
As illustrated by Example 2

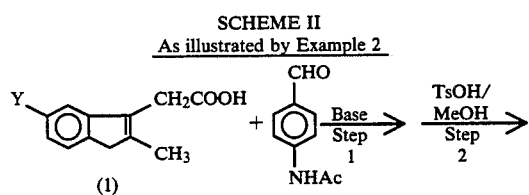

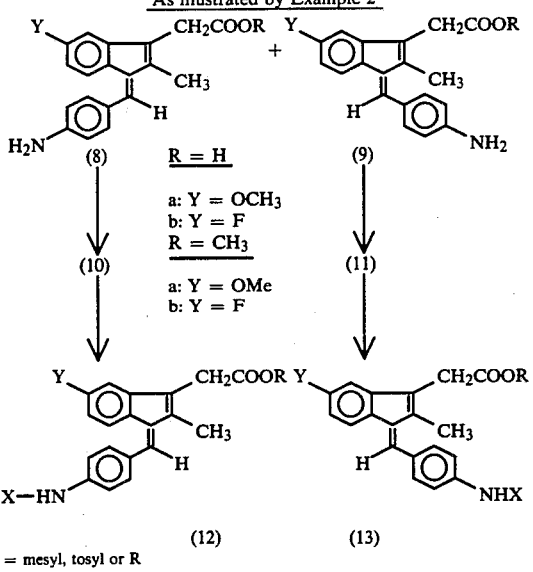

X = mesyl, tosyl or R

EXAMPLE 2

E and Z 1-(4-Substituted aminophenyl)methylene-5-substituted-2-methyl-1H-3-indenylacetic acids and analogs

Step 1

Preparation of Z 1-(4-aminophenylmethylene-5-fluoro-2-methyl-1H-3-indenylacetic acid (8b)

Following the procedure of Example 1, Step 1, but substituting for the compound 1a and p-aminosulfonyl-benzaldehyde used therein, an equivalent amount of 5-fluoro-2-methyl-3-indenylacetic acid and p-acetamidobenzaldehyde, there was obtained Z 1-(4-aminophenyl)methylene-5-fluoro-2-methyl-1H-3-indenylacetic acid (8b); m.p. 214.0°–215.5° C.

Anal. Calcd for $C_{19}H_{16}FNO_2$: C, 73.77; H, 5.21; N, 4.53; F, 6.14. Found: C, 74.00; H, 5.46; N, 4.22; F, 5.65.

Step 2

Preparation of Z methyl 1-(4-aminophenyl)methylene-5-fluoro-2-methyl-1H-3-indenylacetate (10b)

Following the procedure of Example 1, Step 2, but substituting the compound 3a used therein, an equivalent of 8b, there was obtained Z methyl 1-(4-aminophenyl)methylene-5-fluoro-2-methyl-1H-3-indenylacetate (10b); m.p. 102.5°–103.5° C.

Anal. Calcd for $C_{20}H_{18}FNO_2$: C, 74.29; H, 5.61; N, 4.33; F, 5.88. Found: C, 73.86; H, 5.39; N, 4.47; F, 5.55.

Step 3

Mesylation of 10b to form Z methyl 1-(4-N-mesylaminophenyl))methylene-5-fluoro-2-methyl-1H-3-indenylacetate (12b)

To a solution of compound 10b (100 mg) in methylene chloride (20 ml) was added pyridine (55 mg) at 5°–10° and then methanesulfonylchloride (80 mg) dropwise. The mixture was stirred at room temperature for 3½ hours. Purification of the mixture via preparative tlc gave pure Z methyl 1-(4-(N-mesylaminophenyl))methylene-5-fluoro-2-methyl-1H-3-indenylacetate (12b) (110 mg, 88% yield); m.p. 160°–162° C.

Anal. Calcd for $C_{21}H_{20}FNO_4S$: C, 62.83; H, 5.02; N, 3.49; F, 4.73; S, 7.99. Found: C, 63.12; H, 5.01; N, 3.45; F, 4.58; S, 8.13.

Following similar procedures as described in Example 2, Steps 1–3, there was obtained Z methyl 1-(4-(N-mesylaminophenyl))methylene-5-methoxy-2-methyl-1H-3-indenylacetate (12a); m.p. 159°–160° C.

Anal. Calcd for $C_{22}H_{23}NO_5S$: C, 63.91; H, 5.61; N, 3.39; S, 7.75. Found: C, 63.42; H, 5.50; N, 3.26; S, 8.15.

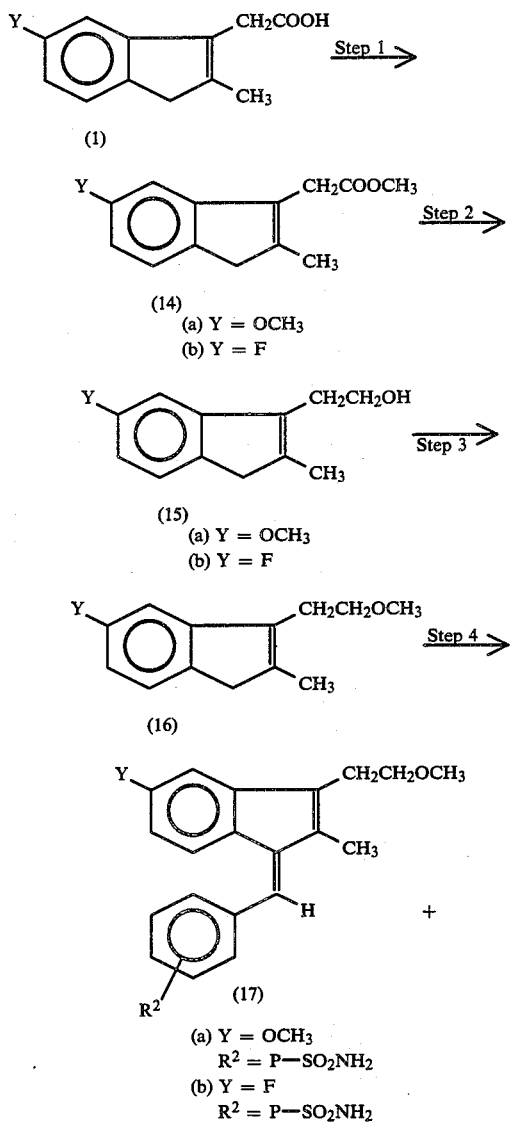

SCHEME III - As illustrated by Example 3

(1)

(14)
(a) Y = OCH₃
(b) Y = F

(15)
(a) Y = OCH₃
(b) Y = F (16)

(17)
(a) Y = OCH₃
  R² = P—SO₂NH₂
(b) Y = F
  R² = P—SO₂NH₂

-continued
SCHEME III - As illustrated by Example 3

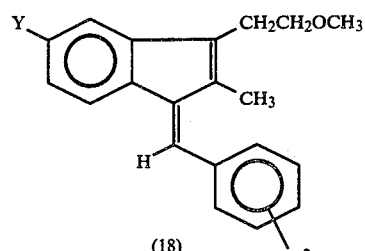

(18)
(a) Y = OMe
  R² = P—SO₂NH₂
(b) Y = F
  R² = P—SO₂NH₂

EXAMPLE 3

E and Z 1-(Substituted phenyl)methylene-5-substituted-2-methyl-1H-3-indenyl-(2-methoxy)ethane

Step 1

Preparation of methyl 5-fluoro-2-methyl-1H-3-indenylacetate (14b)

Following the procedure of Example 1, Step 2, but substituting the compound 3a used therein, an equivalent of 1b, there was produced methyl 5-fluoro-2-methyl-3-indenylacetate (14b) as an oil, which was used in the next step without further purification.

Step 2

LAH reduction of 14b to form 5-fluoro-2-methyl-1H-3-indenyl-(2-hydroxy)ethane (15b)

To a solution of 14b (24 g) in dry THF (300 ml), LiAlH₄ (6.9 g) was added in portions. The mixture was stirred at room temperature for 1.5 hours. Excess LiAlH₄ (LAH) was destroyed with saturated Na₂SO₄ solution. The organic phase was concentrated in vacuo, and the crude product was purified via silica gel column chromatography eluting with methylene chloride. The product was recrystallized from hexane to give 5-fluoro-2-methyl-1H-3-indenyl-(2-hydroxy)ethane (15b) (14.9 g, 63% yield): m.p. 65°–66.5° C.

Anal. Calcd. for $C_{12}H_{13}FO$: C, 74.98; H, 6.82; F, 9.88. Found: C, 74.62; H, 6.64; F, 9.76.

Step 3

Diazomethane methylation of 15b to methyl 5-fluoro-2-methyl-1H-3-indenyl-(2-methoxy)ethane (16b)

To a solution of compound 15b (1.84 g) in methylene chloride (50 ml) containing 5 drops of BF₃-etherate was added a solution of freshly prepared diazomethane ether solution (80 ml, from nitrosomethyl urea). The solution was stirred for ½ hour at room temperature and passed through a short column to remove most of the impurities, and the crude product isolated was used directly in the next step.

Step 4

Preparation of Z and E 1-(4-aminosulfonylphenyl)methylene-5-fluoro-2-methyl-1H-3-indenyl-(2-methoxy)ethane (17b and 18b)

Following the procedure of Example 1, Step 1, but substituting for the compound 1a used therein, an equivalent of 16b, there were produced in 57% yield Z 1-(4-aminosulfonylphenyl)methylene-5-fluoro-2-methyl-1H-3-indenyl-(2-methoxy)ethane (17b), m.p. 145°–147° C.

Anal. Calcd. for $C_{20}H_{20}FNO_3S$: C, 64.33; H, 5.40; N, 3.75; F, 5.09; S, 8.58. Found: C, 64.13; H, 5.19; N, 3.88; F, 5.13; S, 8.47.

and E 1-(4-aminosulfonylphenyl)methylene-5-fluoro-2-methyl-1H-3-indenyl-(2-methoxy)ethane (18b), m.p. 185°–186° C.

Anal. Calcd. for $C_{20}H_{20}FNO_3S$: C, 64.33; H, 5.40; N, 3.75; F, 5.09; S, 8.58. Found: C, 64.06; H, 5.19; N, 3.77; F, 5.17; S, 8.48.

Following the same procedures as described in Step 1-4, the following compounds were prepared:

(1) 5-methoxy-2-methyl-1H-3-indenyl-(2-hydroxy)ethane (15a):

Anal. Calcd. for $C_{13}H_{16}O_2\cdot\frac{1}{4}H_2O$: C, 74.81; H, 7.97. Found: C, 74.46; H, 7.86.

(2) Z 1-(4-aminosulfonylphenyl)methylene-5-methoxy-2-methyl-1H-3-indenyl-(2-methoxy)ethane (17a), m.p. 161.5°–162.5° C.

Anal. Calcd. for $C_{21}H_{23}NO_4S$ C, 65.43; H, 6.01; N, 3.63; S, 8.32. Found: C, 65.27; H, 6.05; N, 3.60; S, 8.25.

(3) E 1-(4-aminosulfonylphenyl)methylene-5-methoxy-2-methyl-1H-3-indenyl-(2-methoxy)ethane (18a), m.p. 138.5°–140.0° C.

Anal. Calcd. for $C_{21}H_{23}NO_4S$ C, 65.43; H, 6.01; N, 3.63; S, 8.32. Found: C, 65.79; H, 6.05; N, 3.62; S, 8.37.

SCHEME IV - As illustrated by Example 4

(15)
a: Y = OCH₃
b: Y = F

(19)
a: Y = OCH₃
b: Y = F

(20)
| | Y | A |
|---|---|---|
| a: | OCH₃ | SCH₃ |
| b: | F | SC₆H₅ |

When R = OCH₃; $R_n^2$ = p-SO$_n$NH₂ (n = 1 or 2)

(21a) A = SCH₃
(22a) A = SCH₃
(23a) A = SC₆H₅
(24a) A = SC₆H₅

(25a) A = —N⌐N⌐ (imidazolyl)

(26a) A = —N⌐N (pyrazolyl)

(27a) A = OH
(28a) A = OH

EXAMPLE 4

E and Z 1-(4-Aminosulfonylphenyl)methylene-5-substituted-2-methyl-1H-3-indenyl-(2-methanesulfonyloxy)ethane Step 1

Preparation of 2-methyl-5-methoxy-1H-3-indenyl-(2-methanesulfonyloxy)ethane (19a)

To a solution of the alcohol 15a (6.0 g) and triethyl amine (6.5 ml) in methylene chloride (60 ml) at room temperature was added a solution of methanesulfonyl chloride (3.0 ml) in methylene chloride (30 ml) dropwise. The mixture was stirred at room temperature for 30 minutes and the precipitates were removed by filtration. The filtrate was evaporated to dryness and the residue was purified via a silica gel column to give 2-methyl-5-methoxy-1H-3-indenyl-(2-methanesulfonyloxy)ethane (19a) (5.7 g, 68% yield): m.p. 84.5°–86.0° C.

Anal. Calcd. for $C_{14}H_{18}O_4S$: C, 59.57; H, 6.43; S, 11.36. Found: C, 59.34; H, 6.64; S, 11.34.

Following the same procedure of Step 1 but starting with 15b, there was prepared 5-fluoro-2-methyl-1H-3-indenyl-(2-methanesulfonyloxy)ethane (19b): m.p. 65.0°–66.5° C.

Anal. Calcd. for $C_{12}H_{13}OF$: C, 74.98; H, 6.82; F, 9.88. Found: C, 74.62; H, 6.64; F, 9.76.

Step 2

Preparation of 2-methyl-5-methoxy-1H-3-indenyl-(2-methylthio)ethane (20a)

To a saturated solution of methyl mercaptan in absolute ethanol (50 ml) containing potassium tert-butoxide (0.994 g) was added the mesylate 19a (2.5 g). The reaction mixture was refluxed for 30 minutes and evaporated to dryness. The residue was purified via preparative tlc using 1500 μm silica gel plates developed with 20% hexane in methylene chloride to give pure 2-methyl-5-methoxy-1H-3-indenyl-(2-methylthio)ethane (20a) (1.79 g, 86% yield).

Following the same procedure of Step 2, 19b was converted by reaction with phenylmercaptan to 5-fluoro-2-methyl-1H-3-indenyl-(2-phenylthio)ethane (20b).

Anal. Calcd. for $C_{19}H_{20}OS.1/6H_2O$: C, 76.21; H, 6.79; S, 10.71. Found: C, 76.18; H, 6.78; S, 10.67.

Step 3

Preparation of Z and E 1-(4-aminosulfonylphenyl)methylene-5-methoxy-2-methyl-1H-3-indenyl-(2-methylthio)ethane (21a and 22a)

Following the procedure of Example 1, Step 1, but substituting the compound 1a used therein an equivalent amount of 20a, there was obtained Z 1-(4-aminosulfonylphenyl)methylene-5-methoxy-2-methyl-1H-3-indenyl-(2-methylthio)ethane (21a): m.p. 178.5°–180.5° C.

Anal. Calcd. for $C_{21}H_{23}NO_3S_2$: C, 62.82; H, 5.77; N, 3.49; S, 15.97. Found: C, 62.52; H, 5.79; N, 3.36; S, 15.94.

and E 1-(4-aminosulfonylphenyl)methylene-5-methoxy-2-methyl-1H-3-indenyl-(2-methylthio)ethane (22a): m.p. 172.5°–173.5° C.

Anal. Calcd. for $C_{21}H_{23}NO_3S_2$: C, 62.82; H, 5.77; N, 3.49; S, 15.97. Found: C, 62.79; H, 5.85; N, 3.44; S, 15.84.

Following the same procedures as described in Steps 1–3, there were prepared the following compounds:

(1) Z 1-(4-aminosulfonylphenyl)methylene-5-methoxy-2-methyl-1H-3-indenyl-(2-phenylthio)ethane (23a).

Anal. Calcd. for $C_{26}H_{25}NO_3S_2.\frac{1}{4}H_2O$: C, 66.71; H, 5.47; N, 2.99. Found: C, 66.86; H, 5.35; N, 3.09.

(2) E 1-(4-aminosulfonylphenyl)methylene-5-methoxy-2-methyl-1H-3-indenyl-(2-phenylthio)ethane (24a).

Anal. Calcd. for $C_{26}H_{25}NO_3S_2.\frac{1}{2}H_2O$: C, 66.07; H, 5.50; N, 2.96. Found: C, 66.15; H, 5.34; N, 3.09.

(3) Z 1-(4-aminosulfonylphenyl)methylene-5-methoxy-2-methyl-1H-3-indenyl-[2-(N-imidazolyl)]ethane (25a): m.p. 240.0°–242.0° C.

Anal. Calcd. for $C_{23}H_{23}N_3O_3S$: C, 65.54; H, 5.50; N, 9.97; S, 7.66. Found: C, 65.63; H, 5.41; N, 9.78; S, 7.62.

(4) E 1-(4-aminosulfonylphenyl)methylene-5-methoxy-2-methyl-1H-3-indenyl-[2-(N-imidazolyl]ethane (26a): m.p. 197.0°–199.0° C.

Anal. Calcd. for $C_{23}H_{23}N_3O_3S.H_2O$: C, 62.86; H, 5.69; N, 9.57. Found: C, 62.75; H, 5.24; N, 9.43.

(5) Z 1-(4-aminosulfonyl)methylene-5-methoxy-2-methyl-1H-3-indenyl-(2-hydroxy)ethane (27a): m.p. 170.0°–171.5° C.

Anal. Calcd. for $C_{20}H_{21}NO_4S.\frac{1}{4}H_2O$: C, 63.90; H, 5.76; N, 3.72. Found: C, 64.06; H, 5.74; N, 3.57.

(6) E 1-(4-aminosulfonyl)methylene-5-methoxy-2-methyl-1H-3-indenyl-(2-hydroxy)ethane (28a): m.p. 185.5°–187.0° C.

Anal. Calcd. for $C_{20}H_{21}NO_4S.\frac{1}{3}H_2O$: C, 63.64; H, 5.78; N, 3.71. Found: C, 63.35; H, 5.88; N, 3.33.

SCHEME V - As illustrated by Example 5

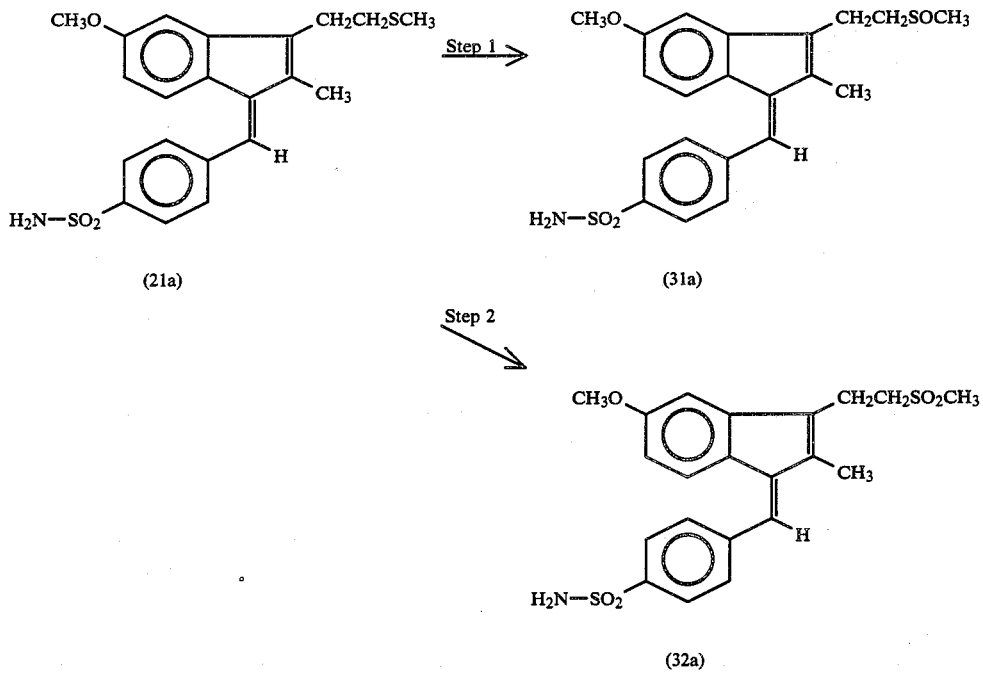

-continued
SCHEME V - As illustrated by Example 5

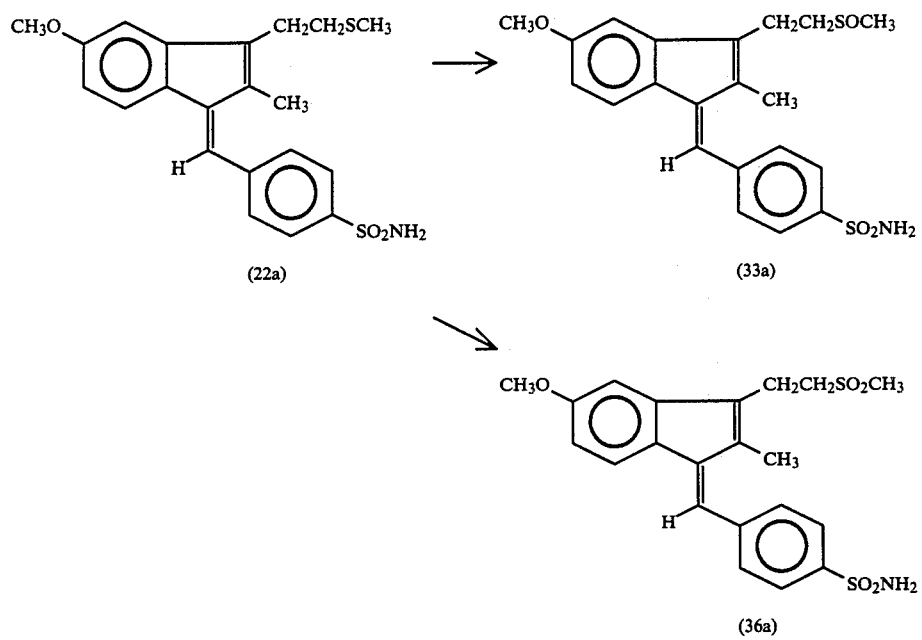

EXAMPLE 5

E and Z
1-(4-Aminosulfonylphenyl)methylene-5-methoxy-2-methyl-1H-3-indenyl-(2-methylsulfinyl)-and-(2-methylsulfonyl)ethanes

Step 1

Preparation of Z
1-(4-aminosulfonylphenyl)methylene-5-methoxy-2-methyl-1H-3-indenyl-(2-methylsulfinyl)ethane (31a)

To a solution of 21a (250 mg) in methanol (35 ml) at 0°–5° C. was added a solution of m-chloroperbenzoic acid (90 mg) in methanol (3 ml). The solution was stirred at 5° C. for ½ hour and room temperature for 1 hour. Purification of the crude product via preparative tlc 1000 mm silica gel plates developed three times with 2.5% methanol in methylene chloride gave pure Z 1-(4-aminosulfonylphenyl)methylene-5-methoxy-2-methyl-1H-3-indenyl-(2-methylsulfinyl)ethane (31a) (140 mg, 54% yield): m.p. 205.0°–207.0° C.

Anal. Calcd. for $C_{21}H_{23}NO_4S_2.H_2O$: C, 57.90; H, 5.78; N, 3.22; S, 14.71. Found: C, 58.08; H, 5.33; N, 3.28; S, 14.67.

Step 2

Preparation of Z
1-(4-aminosulfonylphenyl)methylene-5-methoxy-2-methyl-1H-3-indenyl-(2-methoxysulfonyl)ethane (32a)

Following the procedure of Example 5, Step 1, but substituting one equivalent of MCPBA used therein, two equivalent of MCPBA there was obtained Z 1-(4-aminosulfonylphenyl)methylene-5-methoxy-2-methyl-1H-3-indenyl-(2-methylsulfonyl)ethane (32a): m.p. 181.0°–182.5° C.

Anal. Calcd. for $C_{21}H_{23}NO_5S_2.1/5H_2O$: C, 57.70; H, 5.40; N, 3.21. Found: C, 57.55; H, 5.51; N, 3.30.

Following the same procedures as described in Example 5, Steps 1–2, but starting with the E form (22a), there were prepared the following compounds:

(1) E 1-(4-aminosulfonylphenyl)methylene-5-methoxy-2-methyl-1H-3-indenyl-(2-methylsulfinyl)ethane (33a): m.p. 189.0°–190.5° C.

Anal. Calcd. for $C_{21}H_{23}NO_4S_2.1/5H_2O$: C, 59.89; H, 5.60; N, 3.33; S, 15.23. Found: C, 60.00; H, 5.40; N, 3.61; S, 15.14.

(2) E 1-(4-aminosulfonylphenyl)methylene-5-methoxy-2-methyl-1H-3-indenyl-(2-methylsulfonyl)ethane (34a): m.p. 190.0°–192.0° C.

Anal. Calcd. for $C_{21}H_{23}NO_5S_2.1/5H_2O$: C, 57.70; H, 5.40; N, 3.21. Found: C, 57.74; H, 5.17; N, 3.07.

SCHEME VI - As illustrated by Example 6

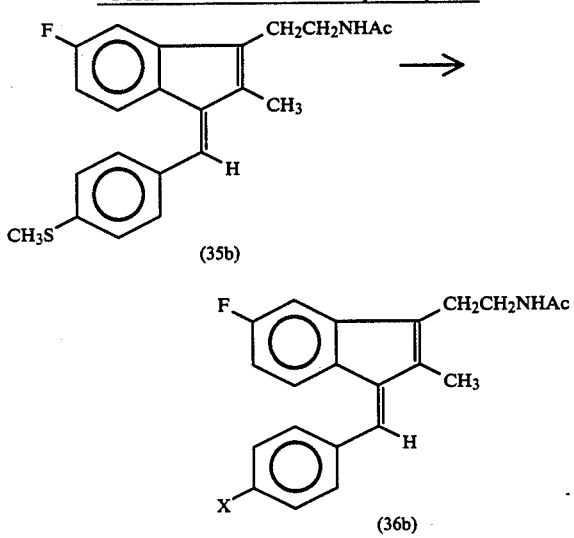

b: X = SOCH₃
c: X = SO₂CH₃

-continued
SCHEME VI - As illustrated by Example 6

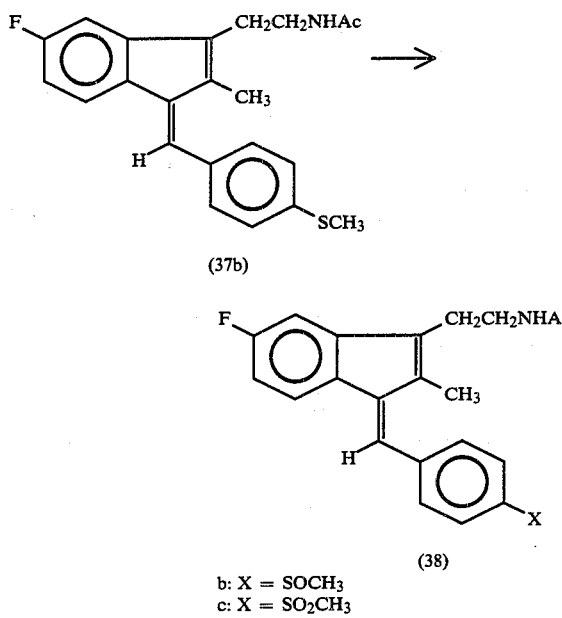

(37b)

b: X = SOCH$_3$
c: X = SO$_2$CH$_3$

EXAMPLE 6

E and Z 1-(4-Substitutedphenyl)methylene-5-fluoro-2-methyl-1H-3-indenyl-(2-acetamido)ethanes Step 1

Preparation of Z 1-(4-methylsulfinylphenyl)methylene-5-fluoro-2-methyl-1H-3-indenyl-2-acetamido)ethane (36b)

Following the procedure of Example 5, Step 1, but substituting the compound 21a used therein, an equivalent amount of 35b, there was produced compound Z 1-(4-methylsulfinylphenyl)methylene-5-fluoro-2-methyl-1H-3-indenyl-(2-acetamido)ethane (36b): m.p. 135°–137° C.

Anal. Calcd. for C$_{22}$H$_{22}$FNO$_2$S.½H$_2$O: C, 67.06; H, 5.90; N, 3.56. Found: C, 67.04; H, 5.54; N, 3.35.

Step 2

Preparation of Z 1-(4-methylsulfonylphenyl)methylene-5-fluoro-2-methyl-1H-3-indenyl-(2-acetamido)ethane (36c)

Following the procedure of Example 5, Step 2, but substituting the compound 21a used therein, an equivalent amount of 35b there was produced Z 1-(4-methylsulfonylphenyl)methylene-5-fluoro-2-methyl-1H-3-indenyl-(2-acetamido)ethane (36c): m.p. 193.5°–194.5° C.

Anal. Calcd. for C$_{22}$H$_{22}$FNO$_3$S: C, 66.14; H, 5.55; N, 3.51; F, 4.76; S, 8.03. Found: C, 66.17; H, 5.56; N, 3.55; F, 4.86; S, 8.32.

Similarly by employing the same procedures as described above, there was prepared the following compound.

· (1) E 1-(4-methylsulfonylphenyl)methylene-5-fluoro-2-methyl-1H-3-indenyl-(2-acetamido)ethane (38c): m.p. 213.5°–215.0° C.

Anal. Calcd. for C$_{22}$H$_{22}$FNO$_3$S: C: 66.14; H, 5.55; N, 3.51; F, 4.76; S, 8.03. Found: C, 66.16; H, 5.54; N, 3.59; F, 4.66; S, 8.03.

SCHEME VII: Photoisomerization as illustrated by Example 7

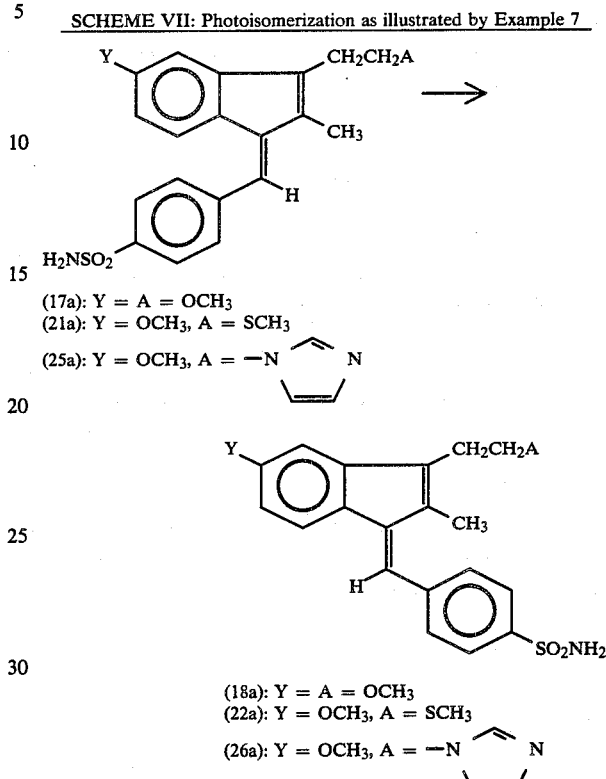

(17a): Y = A = OCH$_3$
(21a): Y = OCH$_3$, A = SCH$_3$
(25a): Y = OCH$_3$, A = —N⌒N (18a): Y = A = OCH$_3$
(22a): Y = OCH$_3$, A = SCH$_3$
(26a): Y = OCH$_3$, A = —N⌒N

EXAMPLE 7

Photoisomerization of Z form indenes to E form indenes

Method A

A solution of the Z methyl ether, Z 1-(4-aminosulfonylphenyl)methylene-5-methoxy-2-methyl-1H-3-indenyl-(2-methoxy)ethane (17a) (650 mg) and benzophenone (2.0 g) in acetonitrile was degassed 2-3 times in a pyrex round-bottomed flask and irradiated with a 3000 Å lamp under nitrogen for 89 hours. The resulting photolysate was purified via preparative tlc using 1000 μm silica gel plate (40 mg per plate) developed 3-5 times with 3% acetone in methylene chloride to give E 1-(4-aminosulfonylphenyl)methylene-5-methoxy-2-methyl-1H-3-indenyl-(2-methoxy)ethane (18a): (66 mg, 10% yield): m.p. 138.5°–140.0° C.

Anal. Calcd. for C$_{21}$H$_{23}$NO$_4$S: C, 65.43; H, 6.01; N, 3.63; S, 8.32. Found: C, 65.09; H, 6.08; N, 3.53; S, 8.16.

Method B

A solution of the Z methyl ether, E 1-(4-aminosulfonylphenyl)methylene-5-methoxy-2-methyl-1H-3-indenyl-(2-methoxy)ethane (17a) (700 mg) and benzophenone (3.5 g) was irradiated with a medium pressure Hanovia lamp (450 watt) through a quartz well for 75 minutes under nitrogen. Following the work up procedure of Method A, there was obtained E 1-(4-aminosulfonylphenyl)methylene-5-methoxy-2-methyl-1H-3-indenyl-(2-methoxy)ethane (18a) (90 mg, 13% yield): m.p. 139.5°–140.0° C.

Anal. Calcd. for $C_{21}H_{23}NO_4S$: C, 65.43; H, 6.01; N, 3.63; S, 8.32. Found: C, 65.30; H, 5.99; N, 3.62; S, 8.31.

Similarly, the Z imidazol derivative, 1-(4-aminosulfonylphenyl)methylene-5-methoxy-2-methyl-1H-3-indenyl-[2-(N-imidazolyl)]ethane (25a) was converted to E 1-(4-aminosulfonylphenyl)methylene-5-methoxy-2-methyl-1H-3-indenyl-[2(N-imidazolyl)]ethane (26a); m.p. 216.0°–217.0° C.

Anal. Calcd. $C_{23}H_{23}N_3O_3S$: C, 65.54; H, 5.50; N, 9.97; S, 7.66. Found: C, 65.22; H, 5.52; N, 9.87; S, 7.45.

C. Utility of the compounds within the scope of the invention

This invention also relates to a method of treatment for patients (or mammalian animals raised in the diary, meat, or fur industries or as pets) suffering from disorders or diseases which can be attributed to PAF as previously described, and more specifically, a method of treatment involving the administration of compound (I) as the active constituent.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by the PAF, compound (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order from about 1 mg to about 100 mg per kilogram of body weight per day are useful in the treatment of the above-indicated conditions (from about 50 mg to about 5 gms. per patient per day). For example, inflammation is effectively treated and anti-pyretic and analgesic activity manifested by the administration from about 25 to about 75 mg of the compound per kilogram of body weight per day (about 75 mg to about 3.75 gms per patient per day). Advantageously, from about 5 mg to about 50 mg per kilogram of body weight per daily dosage produces highly effective results (about 250 mg to about 2.5 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological Data Supporting the Utility of the Compounds Within the Scope of the Invention It has been found that the compounds of formula (I) exhibit in vitro and in vivo antagonistic activities with respect to the PAF.

A. In Vitro Assay

In vitro, they inhibit PAF-induced functions in both the cellular and tissue levels by disturbing the PAF binding to its specific receptor site. The ability of a compound of formula (I) to inhibit the PAF binding to its specific receptor binding site on rabbit platelet plasma membranes was measured by an assay recently developed by us.

The inhibition of $H^3$-PAF binding to the rabbit platelet plasma membrane by a PAF-antagonist of Formula (I) was determined by a method employing isotropic labeling and filtration techniques. Generally, a series of Tris-buffered solutions of the selected antagonist at predetermined concentrations were prepared. Each of these solutions contains 1 pmole of $^3$H-PAF, a known amount of the test antagonist, and a sufficient amount of the pH 7.5 Tris-buffer solution (10 mM Tris, 0.25% bovine serum albumin, and 150 mM NaCl per ml water) to make the final volume of 1 ml. After adding into a set of test tubes each with 100 µg of the platelet plasma membrane suspension (S. B. Hwang, et al., *Biochemistry*, 22, 4756 (1983)) and one of the Tris-buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains $C_1$ plus a 1000-fold excess of unlabeled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0°–5° C.) Tris-buffer solution. Each washed residue was then suspended in 10 ml scintillation solution (Aquasol 2, New England Nuclear, Connecticut) and the radioactivity was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non-specific binding $C_2$", the percent inhibition of each test antagonist can be determined by the following equation:

$$\% \text{ Inhibition} = \frac{(\text{Total binding } C_1) - (\text{Total binding with antagonist})}{\text{Specific binding}} \times 100$$

Specific binding = (Total binding $C_1$) − (non-specific binding $C_2$)

The following Tables I and II summarize the in vitro results:

TABLE 1

% Inhibition of PAF Binding by
E (Trans)-1-(4-Substituted phenyl)methylene-5-$R^3$—2-methyl-3-indenyl-$R^1$.

| $R^1$ | $R^2$ | $R^3$ | Dose μM | % Inhibitor |
|---|---|---|---|---|
| $CH_2COOCH_3$ | $SO_2NH_2$ | $OCH_3$ | 5 | 100 |
| | | | 1 | 84 |
| | | | 0.5 | 70 |
| | | | 0.1 | 35 |
| $CH_2COOCH_3$ | $SO_2NHCH_3$ | $OCH_3$ | 5 | 100 |
| | | | 0.5 | 67 |
| $CH_2COOCH_3$ | $SOCH_3$ | F | 5 | 45 |
| $CH_2COOCH_3$ | $SO_2NH_2$ | F | 1 | 60 |
| $CH_2COOCH_3$ | $SO_2NHCH_3$ | F | 1 | 56 |
| $CH_2CH_2OH$ | $SO_2NH_2$ | $OCH_3$ | 1 | 59 |
| $CH_2COOCH_3$ | 3,4-dimethoxy | $OCH_3$ | 10 | 87 |
| | | | 1 | 45 |
| $CH_2COOH$ | $SO_2NH_2$ | $OCH_3$ | 5 | 4 |
| $CH_2CH_2OCH_3$ | $SO_2NH_2$ | $OCH_3$ | 5 | 100 |
| | | | 2.5 | 100 |
| | | | 1 | 80 |
| | | | 0.5 | 76 |
| | | | 0.25 | 58 |
| | | | 0.1 | 40 |
| | | | 0.05 | 20 |
| | | | 0.1 | 2 |
| $CH_2CH_2SOCH_3$ | $SO_2NH_2$ | $OCH_3$ | 5 | 74 |
| | | | 0.5 | 24 |
| $CH_2CH_2SCH_3$ | $SO_2NH_2$ | $OCH_3$ | 1 | 100 |
| | | | 1 | 100 |
| | | | 0.5 | 78 |
| | | | 0.1 | 34 |
| $CH_2CH_2SO_2CH_3$ | $SO_2NH_2$ | $OCH_3$ | 5 | 100 |
| | | | 1 | 81 |
| | | | 0.5 | 61 |
| | | | 0.1 | 35 |
| $CH_2CH_2SC_6H_5$ | $SO_2NH_2$ | $OCH_3$ | 5 | 56 |
| $CH_2CH_2$—N⟨=⟩N (imidazolyl) | $SO_2NH_2$ | $OCH_3$ | 5 | 90 |
| | | | 1 | 45 |
| | | | 0.5 | 31 |
| | | | 0.1 | 17 |
| $CH_2CH_2OCH_3$ | $SO_2NH_2$ | F | 5 | 61 |

TABLE II

% Inhibition of PAF Receptor by
Z(Cis) 1-(4-Substituted-phenyl)methylene-5-$R^3$—2-methyl-3-indenyl-$R^1$

| $R^1$ | $R^2$ | $R^3$ | Dose μM | % Inhibitor |
|---|---|---|---|---|
| $CH_2CH_2NHCOCH_3$ | $SCH_3$ | F | 5 | 50 |
| $CH_2CH_2NHCOCH_3$ | $SOCH_3$ | F | 5 | 39 |
| $CH_2CH_2NHCOCH_3$ | $SO_2CH_3$ | F | 5 | 68 |
| | | | 5 | 90 |
| $CH_2COOH$ | $SO_2NH_2$ | $OCH_3$ | 50 | 94 |
| | | | 20 | 57 |
| | | | 5 | 32 |
| $CH_2COOCH_3$ | $SONH$—$C(NH)NH_2$ | $OCH_3$ | 1 | 50 |
| $CH_2COOCH_3$ | —$NHSO_2$—$CH_3$ | $OCH_3$ | 10 | 72 |
| | | | 3 | 35 |
| $CH_2COOH$ | —$SOCH_3$ | $OC_2H_5$ | 5 | 42 |
| $CH_2CH_2SC_6H_5$ | —$SO_2NH_2$ | $OCH_3$ | 5 | 33 |
| $CH_2COOCH_3$ | —$SO_2NH_2$ | $OCH_3$ | 50 | 100 |
| | | | 20 | 100 |
| | | | 10 | 75 |
| | | | 5 | 66 |
| | | | 3 | 58 |
| | | | 1 | 39 |
| $CH_2CH_2OCH_3$ | —$SO_2NH_2$ | F | 5 | 29 |
| $CH_2CH_2$—N⟨=⟩N (imidazolyl) | —$SO_2NH_2$ | $OCH_3$ | 5 | 68 |
| $CH_2CH_2SOCH_3$ | $SO_2NH_2$ | $OCH_3$ | 5 | 56 |

B. In Vivo Assay

The specific PAF-antagonistic activities are further established by in vivo assays following the protocol (modified procedure of Humphrey et al., *Lab. Investigation*, 46, 422 (1982)) described below:

Protocol for the Evaluation of the Oral Activity of PAF Antagonists or the Inhibition of PAF-Induced Increase of Vasopermeability by PAF-Antagonists I. Animal species: 5 guinea pigs (400–500 g)
II. Material:
0.5% (w/v) aqueous methylcellulose solution
sodium nembutol
2% Evans Blue solution: 2 g of Evans Blue in 100 ml of pH 7.5 Tris-Buffer solution
Tris-Buffer solution: 150 mM NaCl and 10 mM Tris/ml with pH adjusted to 7.5.

III. Procedure
(1.) Weigh the guinea pigs. Label them as control. $T_1$, $T_2$, $T_3$ and $T_4$.
(2.) Fast the animals overnight.
(3.) Weigh the animals again after the fasting.
(4.) Ground and suspend a PAF antagonist of formula (I) with intensive sonication in 3 ml of 0.5% aqueous methylcellulose solution.
(5.) Administer orally to each of the animals $T_1$, $T_2$, $T_3$ and $T_4$ an appropriate amount (in terms of mg/kg of bodyweight) of the antagonist solution from 4), except the control animal which should receive only the 0.5% aq. methylcellulose solution.
(6.) Forty minutes after the oral administration,

| Protocol for the Evaluation of the Oral Activity of PAF Antagonists or the Inhibition of PAF-Induced Increase of Vasopermeability by PAF-Antagonists |
|---| anesthetize the animals with sodium nembutol (0.75 ml/kg i.p.).

(7.) After 20 minutes or when the anesthetics became effective, inject intracardially to each animal 2 ml/kg body weight of the 2% Evans Blue solution.

(8.) Wait for 10 minutes. In the meantime, shave the backs of the guinea pigs and get ready for the PAF injection. Select two rows of 5 (a total of ten) sites on the back of each animal and designate them as sites

| 1a | 2a | 3a | 4a | 5a |
| 1b | 2b | 3b | 4b | 5b | and inject intracutaneously, in duplicate 0.1 ml of a PAF solution in Tris-buffer or 0.1 ml of the Tris-buffer itself (control) according to the following schedule:

| Sites | Solution to be injected |
|---|---|
| 1a | Tris-buffer |
| 1b | " |
| 2a | $5 \times 10^{-9}$ g/ml PAF |
| 2b | " |
| 3a | $5 \times 10^{-8}$ g/ml PAF |
| 3b | " |
| 4a | $5 \times 10^{-7}$ g/ml PAF |
| 4b | " |
| 5a | $5 \times 10^{-6}$ g/ml PAF |
| 5b | " |

Repeat the same injection on the backs of the remaining animals.

(9.) Wait for 30 minutes or until the blue color developed into a steady shade on each injection site. Open the chest of each animal, extract by cardiac puncture 1 ml of blood and transfer it to a marked centrifuge tube. Centrifuge all the five blood samples at about 2000 xg for 10 minutes and decant the blue tinted supernatants (plasma). Set aside these plasma samples for later spectroscopic measurements.

(10.) Sacrifice the animals and remove the back skin of each of them. Isolate with a 20 mm diameter steel punch the injection sites (blue spots) into individual discs of skin and dissect each of the skin discs into about 10-20 pieces.

(11.) Mix in a 50 ml polyethylene test tube the skin pieces from a particular injection site with a medium containing 14 ml of acetone and 6 ml of 0.5% aqueous solution of sodium sulfate. See Harada, M., et al., J. Pharm. Pharmacol. 23, 218-219 (1971) for detailed procedures. Repeat the same procedures for each individual injection site.

(12.) Homogenize the contents of each test tube on a polytron (Kinematica GmbH, Switzerland) with setting at 5 for 10-20 seconds.

(13.) In the meantime, extract a 100 μl sample of each of the plasma set aside in Step (9) with the same acetone-aqueous sodium sulfate solution used in Step (11). Set aside the resulting extracts for late determination of the Evans blue concentration in the plasma of each animal.

(14.) Centrifuge the skin preparations from Step (12) for 10 minutes at 750 xg and decant the supernatants for the following spectroscopic determination.

(15.) Measure the absorbance of each supernatant from Step (14) ("skin sample") as well as the plasma extract from Step (13) ("plasma sample") at 620 nm with a Cary 210 spectrophotometer (Varian, Palo Alto, CA). Calculate the amount of Evans blue in each skin sample in terms of the volume (μl) of the exuded blood plasma according to the following equation:

| Protocol for the Evaluation of the Oral Activity of PAF Antagonists or the Inhibition of PAF-Induced Increase of Vasopermeability by PAF-Antagonists |
|---|

$$\text{Exuded plasma at a particular injection site (μl)} = \frac{\text{Absorbance (at 620 nm) of "skin sample"}}{\text{Absorbance (at 620 nm) of "plasma sample" of the same animal}} \times 100 \quad \text{(II)}$$

(16.) Draw a plasma exudation curve for each animal, i.e., control, $T_1$, $T_2$, $T_3$ and $T_4$.

(17.) Calculate the percent inhibition of PAF-induced cutaneous vascular permeability from measuring the area under the plasma exudation curve of the control animal ($A_C$) and that of an animal treated orally with an antagonist ($A_D$), for example $T_1$, according to the following equation:

% inhibition observed from the guinea pig $T_1$ treated with x mg/kg of antagonist X. = % inhibition at x mg/kg dosage level of antagonist X.

$= A_C - A_D/A_C \times 100$
$= (1 - A_D/A_C) \times 100$ where the ratio $A_D/A_C$ can be determined from the weight of the paper under the plasma exudation curve of the control curve (A) and that under the plasma exudation curve of the treated animal $T_1$ ($A_D$).

The following table summarized the in vivo results.

TABLE III

% In Vivo Inhibition of PAF Receptor by E (Trans)-1-(4-Substitutedphenyl)-methylene-5-$R^3$—-2-methyl-1H—3-indenyl-$R^1$:

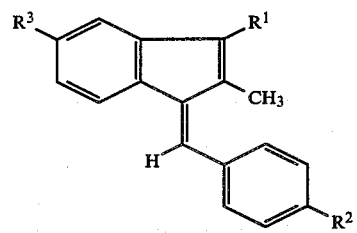

| $R^1$ | $R^2$ | $R^3$ | Dose mg/kg | % Inhibitor |
|---|---|---|---|---|
| $CH_2CH_2OCH_3$ | $SO_2NH_2$ | $OCH_3$ | 30 | 67 |
|  |  |  | 20 | 60 |
|  |  |  | 10 | 28 |
| $CH_2CH_2SO_2CH_3$ | $SO_2NH_2$ | $OCH_3$ | 20 | 45 |
|  |  |  | 10 | 9 |
| $CH_2CH_2SCH_3$ | $SO_2NH_2$ | $OCH_3$ | 20 | 46 |
|  |  |  | 10 | 30 |
| $CH_2COOCH_3$ | $SO_2NH_2$ | $OCH_3$ | 50 | 0 |
| $CH_2CH_2-N\overset{\frown}{\phantom{xx}}N$ | $SO_2NH_2$ | $OCH_3$ | 50 | 59 |
|  |  |  | 45 | 52 |

What is claimed is:

1. A compound of formula:

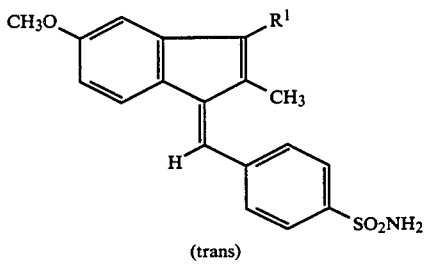

(trans)

wherein R¹ is
(a) CH₂COOCH₃
(b) CH₂CH₂OH
(c) CH₂CH₂OCH₃
(d) CH₂CH₂SCH₃
(e) CH₂CHSC₂H₅
(f) CH₂CH₂SC₆H₅
(g) CH₂CH₂SOCH₃.

2. A pharmaceutical composition for the treatment of a PAF-mediated disease comprising a pharmaceutical carrier and a therapeutically effective amount of a compound of formula:

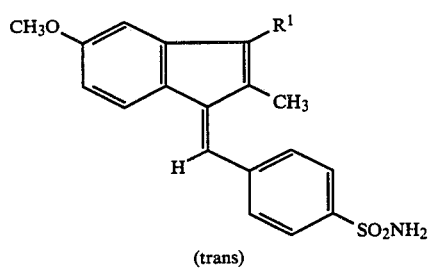

(trans)

wherein R¹ is
(a) CH₂COOCH₃
(b) CH₂CH₂OH
(c) CH₂CH₂OCH₃
(d) CH₂CH₂SCH₃
(e) CH₂CHSC₂H₅
(f) CH₂CH₂SC₆H₅
(g) CH₂CH₂SOCH₃.

3. A method for treating a PAF-mediated disease comprising the administration to a mammalian species in need of such treatment a therapeutically effective amount of a compound of formula:

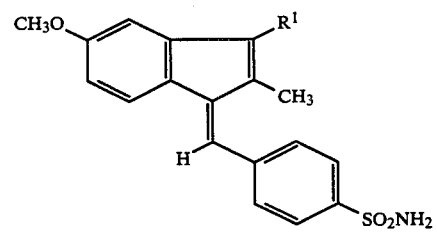

(trans)

wherein R¹ is
(a) CH₂COOCH₃
(b) CH₂CH₂OH
(c) CH₂CH₂OCH₃
(d) CH₂CH₂SCH₃
(e) CH₂CHSC₂H₅
(f) CH₂CH₂SC₆H₅
(g) CH₂CH₂SOCH₃.

4. A compound of formula

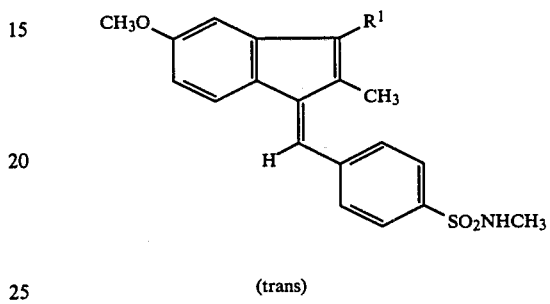

(trans)

wherein R¹ is CH₂COOCH₃.

5. A pharmaceutical composition for the treatment of a PAF-mediated disease comprising a pharmaceutical carrier and a therapeutically effective amount of a compound according to claim 4.

6. A method for treating a PAF-mediated disease comprising the administration to a mammalian species in need of such treatment a therapeutically effective amount of a compound according to claim 4.

7. A compound of formula

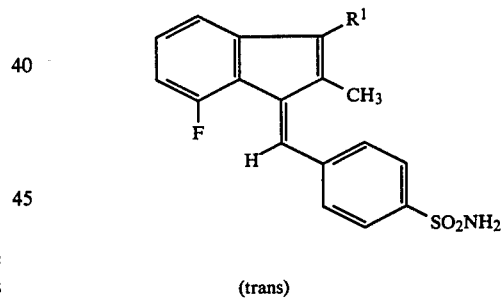

(trans)

wherein R¹ is
(a) CH₂CH₂CH₂CH₂CH₃
(b) CH₂CH₂OCH₃.

8. A pharmaceutical composition for the treatment of a PAF-mediated disease comprising a pharmaceutical carrier and a therapeutically effective amount of a compound according to claim 7.

9. A method for treating a PAF-mediated disease comprising the administration to a mammalian species in need of such treatment a therapeutically effective amount of a compound according to claim 7.

* * * * *